(12) United States Patent
Dussarrat

(10) Patent No.: US 8,329,583 B2
(45) Date of Patent: Dec. 11, 2012

(54) METAL PRECURSORS FOR SEMICONDUCTOR APPLICATIONS

(75) Inventor: Christian Dussarrat, Wilmington, DE (US)

(73) Assignee: L'Air Liquide, Société Anonyme pour l'Etude et l'Exploitation des Procédés Georges Claude, Paris (FR)

(*) Notice: Subject to any disclaimer, the term of this patent is extended or adjusted under 35 U.S.C. 154(b) by 0 days.

(21) Appl. No.: 13/094,421

(22) Filed: Apr. 26, 2011

(65) Prior Publication Data

US 2011/0207324 A1 Aug. 25, 2011

Related U.S. Application Data

(63) Continuation of application No. 12/124,360, filed on May 21, 2008, now Pat. No. 7,951,711.

(60) Provisional application No. 60/939,271, filed on May 21, 2007.

(51) Int. Cl.
*H01L 21/44* (2006.01)
*C07F 1/00* (2006.01)

(52) U.S. Cl. .......... 438/686; 556/112; 257/E21.477

(58) Field of Classification Search .......... 438/681, 438/686; 427/255.23, 255.31; 257/E21.16, 257/E21.477; 556/112
See application file for complete search history.

(56) References Cited

U.S. PATENT DOCUMENTS

| | | | |
|---|---|---|---|
| 3,185,718 A | 5/1965 | Brown et al. | |
| 4,880,670 A | 11/1989 | Erbil | |
| 5,098,516 A | 3/1992 | Norman et al. | |
| 5,130,172 A | 7/1992 | Hicks et al. | |
| 5,306,836 A | 4/1994 | Purdy | |
| 5,352,488 A * | 10/1994 | Spencer et al. | 427/250 |
| 5,441,766 A | 8/1995 | Choi et al. | |
| 5,767,301 A | 6/1998 | Senzaki et al. | |
| 6,420,582 B1 * | 7/2002 | Okamoto | 556/136 |
| 7,045,457 B2 | 5/2006 | Machida et al. | |
| 2003/0100162 A1 | 5/2003 | Joo | |
| 2003/0129826 A1 | 7/2003 | Werkhoven et al. | |
| 2003/0207564 A1 | 11/2003 | Ahn et al. | |
| 2004/0129212 A1 | 7/2004 | Gadgil et al. | |
| 2005/0120475 A1 | 6/2005 | Englefield et al. | |
| 2006/0223300 A1 | 10/2006 | Simka et al. | |
| 2008/0318417 A1 * | 12/2008 | Shinriki et al. | 438/650 |

FOREIGN PATENT DOCUMENTS

| | | |
|---|---|---|
| EP | 0 297 348 | 1/1989 |
| JP | 09-235287 * | 9/1997 |
| WO | WO 2005 020317 | 3/2005 |
| WO | WO 2007 140813 | 12/2007 |
| WO | WO 2007 141059 | 12/2007 |

OTHER PUBLICATIONS

D. W. Macomber, et al, "Cyclopentadienyl and Pentamethylcyclopentadienyl copper compounds containing Phosphine, Carbonyl, and Acetylinic Ligands" J. Am. Chen. Soc., (1983) vol. 105, pp. 5325-5329.*
D. N. Akbayeva, "Cu(I) an dRu(II) complexes with elemental Phospine as ligand: synthesis and properties", Russ. J. of Coordination Chem. (2006), vol. 32, No. 5, pp. 329-334.*
Patent Abstracts of Japan, publication No. 09235287, publication date Sep. 9, 1997; application No. 08044764, application date Aug. 1, 1996.
Akbayeva, "Cu(I) and Ru(II) complexes with elemental phosphorus as ligand: Synthesis and properties." Database CA [Online], Chemical Abstracts Service, Columbus, OH, retrieved from STN Database accession No. 2006:473550 & Russian J. of Coordination Chemistry, 32(5), 329-334.
Chi et al., "Chemistry of copper (I) B-diketonate complexes." J. of Organometallic Chemistry, 449 (1993) pp. 181-189.
Choi et al., "Copper(I) tert-Butyl 3-Oxobutanoate complexes as precursors for chemical vapor deposition of copper." Beckman Institute for Advanced Science and Technology, U. of Illinois at Urbana, vol. 10, No. 9, pp. 2326-2328. 1998.
Donnelly et al., "Copper metallorganic chemical vapor deposition reactions of hexafluoroacetylacetonate Cu(I) vinyltrimethylsilane and bis(hexafluoroacetylacetonate) Cu(II) adsorbed on titanium nitride." J. Vac. Sci. Technol. A 11(1) Jan.-Feb. 1993, pp. 66-77.
Dubois et al., "Selectivity and copper chemical vapor deposition." J. Electrochem. Soc., vol. 130, No. 11, Nov. 1992, pp. 3295-3299.
Macomber et al., "($\eta^5$-cyclopentadienyl)- and ($\eta^5$-Pentamethylcyclopentadienyl)copper compounds containing phosphine, carbonyl, and $\eta^2$-acetylenic ligands." J. American Chemical Soc., vol. 105, No. 16, 1983, pp. 5325-5329.
Mansson, "Cyclopentadienylcopper reactions with organic halides in the presence of dimethyl sulfide." ACTA Chemica Scandinavica, Series B: Organic Chemistry and Biochemistry, vol. B32, No. 7, 1978, pp. 543-544.
Nielson et al., "Development of the ReaxFF reactive force field for describing transition metal catalyzed reactions, with application to the initial stages of the catalytic formation of carbon nanotubes." J. of Physical Chemistry A, 109(3), pp. 493-499.
International Search Report and Written Opinion for related PCT/IB20089/052011, Oct. 6, 2008.

* cited by examiner

*Primary Examiner* — Caridad Everhart
(74) *Attorney, Agent, or Firm* — Patricia E. McQueeney

(57) ABSTRACT

Methods and compositions for depositing metal films are disclosed herein. In general, the disclosed methods utilize precursor compounds comprising gold, silver, or copper. More specifically, the disclosed precursor compounds utilize pentadienyl ligands coupled to a metal to increase thermal stability. Furthermore, methods of depositing copper, gold, or silver are disclosed in conjunction with use of other precursors to deposit metal films. The methods and compositions may be used in a variety of deposition processes.

22 Claims, No Drawings

METAL PRECURSORS FOR SEMICONDUCTOR APPLICATIONS

CROSS-REFERENCE TO RELATED APPLICATIONS

The present application is a continuation of U.S. patent application Ser. No. 12/124,360, filed May 21, 2008, now U.S. Pat. No. 7,951,711, which claims the benefit of U.S. Provisional Application Ser. No. 60/939,271, filed May 21, 2007, both of which are herein incorporated by reference in their entireties for all purposes.

BACKGROUND

1. Field of the Invention

This invention relates generally to the field of semiconductor fabrication. More specifically, the invention relates to new precursors for deposition of metal films on to substrates.

2. Background of the Invention

ALD and CVD are particularly useful techniques for deposition of metal films as compared to other methods of deposition such as physical vapor deposition (PVD) methods like sputtering, molecular beam epitaxy, and ion beam implantation. ALD and CVD can also be used to provide flexibility in the design of manufacturing electronic devices including the potential to reduce the number of processing phases required to provide a desired product. These techniques allow conformal deposition, selective deposition for the deposition of copper, silver, gold and other materials. Suitable processes to form metal films require the identification of relevant precursors requiring strict requirements such as being thermally stable, easily vaporized, reactive, with clean decomposition.

The need for high performance interconnection materials increases as device feature sizes shrink and device density increases. Copper provides an alternative to CVD of aluminum in ultra large scale integrated (ULSI) devices due to its low resistivity (1.67 $\mu\Omega$cm for Cu, 2.65 $\mu\Omega$cm for Al), high electromigration resistance and high melting point (1083° C. for Cu, 660° C. for Al). Its low interconnect resistivity also may allow for faster devices.

Copper precursors are quite volatile and show low deposition temperatures, but are highly, sensitive to heat and oxygen. The latter precursors are rather stable, but are isolated as solids with high melting points and thus require high deposition temperatures. It is common for impurities such as carbon or oxygen to be incorporated during the thermal CVD process when using certain organometallic precursors. For instance, ($\eta$ 5-C 5H 5)Cu(PMe3) produces copper films leading to incorporation of phosphorus. Moreover, phosphine-containing molecules are disqualified because of their high toxicity. Organic phosphines are very hazardous and PF3 being both hazardous and might lead to undesired phosphorus contamination and fluorine-induced etching/damage. Such chemicals might therefore be subject to strict regulations.

An example of an existing copper precursor includes (1,1,1,5,5,5-hexafluoro-2,4-pentanedionate)CuL ((hfac)CuL), where L is a Lewis base. These types of precursors have been the most studied copper precursors to date because they can deposit copper via a thermal disproportionation reaction. Especially (1,1,1,5,5,5-hexafluoro-2,4-pentanedionate)Cu (trimethylvinylsilane), which has attracted much attention because it is a liquid with reasonably high vapor pressure. Other copper compounds such as (1,1,1,5,5,5-hexafluoro-2,4-pentanedionate)CuL, where L is 1,5-cyclooctadiene (CUD), alkyne or trialkylphosphine, are either solids or liquids with a low vapor pressure. Although (hfac)Cu(trimethylvinylsilane) ((hfac)Cu(tmvs)) has been the most utilized copper precursor, its stability is not satisfactory for the selective growth of copper films with reproducibility. In addition, studies have demonstrated that the chemical vapor deposition reaction of (hfac)Cu(tmvs) under ultra high vacuum conditions produced contamination by carbon and fluorine in the deposited films. Therefore, a precursor with high volatility and stability, which contains no fluorinated ligands, is more desirable for the deposition of copper by CVD.

Copper compounds of acetoacetate derivatives which contain no fluorinated ligands have been previously used as CVD precursors. Although these compounds were reported to be volatile and capable of depositing copper films at low substrate temperatures. The studied acetoacetate derivatives were found to be attractive since they were volatile without employing fluorinated ligands and deposited copper films at temperatures below 200° C. However, these derivatives are solid with high melting points and are incapable of selective deposition of copper. On the other hand, the Cu(I) acetoacetate derivatives deposited copper films at relatively low temperatures via disproportionation reaction. However, few are practical for use as CVD precursors since they are either solids or liquids with a low vapor pressure or they have an extremely low thermal stability (i.e. their decomposition temperature is within a few degrees of their vaporization temperature).

Consequently, there is a need for organometallic precursors to deposit metal film without decomposition of the ligands and without associated toxic by products.

BRIEF SUMMARY

New precursor compositions for metal film deposition are disclosed herein. In general, the disclosed compositions utilize precursor compounds comprising copper, gold, silver, etc. More specifically, the disclosed precursor compounds utilize pentadienyl ligands coupled to a metal (e.g. copper, gold, silver) to increase thermal stability. Furthermore, methods of depositing copper, gold, or silver are disclosed in conjunction with use of other precursors to deposit metal films. The methods and compositions may be used in a variety of deposition processes. The disclosed compounds have several advantages such thermal stability at room temperatures. In addition, the disclosed precursors do not contain toxic phosphorous compounds. Other aspects of the methods and compositions will be described in more detail below.

In an embodiment, a method for depositing a metal film on to one or more substrates comprises providing one or more substrates in a reaction chamber. The method further comprises introducing a first precursor into the reaction chamber, wherein the first precursor comprises an organometallic compound having the formula: $(Op)_x(Cp)_yMR'_{2-x-y}$. M is a group 11 metal. Op is an open-pentadienyl group, Cp is a cyclopentadienyl group, R' is selected from the group consisting of a C1 to C12 alkyl group, a trialkylsilyl group, an alkylamide group, an alkoxide group, an alkylsilyl group, an alkylsilylamide group, an amidinate group, CO, $SMe_2$, $SEt_2$, $SiPr_2$, SMeEt, SMe(iPr), SEt(iPr), $OMe_2$, $OEt_2$, tetrahydrofuran (THF), and combinations thereof. The Op and Cp groups may comprise functional groups selected from the group consisting of a hydrogen group, a halogen group, a C1-C4 alkyl group, an alkylamide group, an alkoxide group, an alkylsilylamide group, an amidinate group, a carbonyl group, and combinations thereof. The subscript "x" is an integer ranging from 0 to 1 and the subscript "y" is an integer ranging from 0 to 1. The method also comprises vaporizing the first precursor to deposit the metal film on to the one or more substrates.

In an embodiment, a precursor for depositing a metal film on to one or more substrates comprises an organometallic compound having the formula:

$$(Op)_x(Cp)_y MR'_{2-x-y}$$

where M is a group 11 metal, Op is an open-pentadienyl group, Cp is a cyclopentadienyl group, R' is selected from the group consisting of a C1 to C12 alkyl group, a trialkylsilyl group, an alkylamide group, an alkoxide group, an alkylsilyl group, an alkylsilylamide group, an amidinate group, CO, $SMe_2$, $SEt_2$, $SiPr_2$, SMeEt, SMe(iPr), SEt(iPr), $OMe_2$, $OEt_2$, tetrahydrofuran (THF), and combinations thereof. The Op and Cp groups may comprise functional groups selected from the group consisting of a hydrogen group, a halogen group, a C1-C4 alkyl group, an alkylamide group, an alkoxide group, an alkylsilylamide group, an amidinate group, a carbonyl group, and combinations thereof. The subscript x is an integer ranging from 0 to 1 and the subscript y is an integer ranging from 0 to 1.

The foregoing has outlined rather broadly the features and technical advantages of the present invention in order that the detailed description of the invention that follows may be better understood. Additional features and advantages of the invention will be described hereinafter that form the subject of the claims of the invention. It should be appreciated by those skilled in the art that the conception and the specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

NOTATION AND NOMENCLATURE

Certain terms are used throughout the following description and claims to refer to particular system components. This document does not intend to distinguish between components that differ in name but not function.

In the following discussion and in the claims, the terms "including" and "comprising" are used in an open-ended fashion, and thus should be interpreted to mean "including, but not limited to . . . ". Also, the term "couple" or "couples" is intended to mean either an indirect or direct chemical bond. Thus, if a first molecule couples to a second molecule, that connection may be through a direct bond, or through an indirect bond via other functional groups or bonds. The bonds may be any known chemical bonds such as without limitation, covalent, ionic, electrostatic, dipole-dipole, etc.

As used herein, the term "alkyl group" refers to saturated functional groups containing exclusively carbon and hydrogen atoms. Further, the term "alkyl group" refers to linear, branched, or cyclic alkyl groups. Examples of linear alkyl groups include without limitation, methyl groups, ethyl groups, propyl groups, butyl groups, etc. Examples of branched alkyls groups include without limitation, t-butyl. Examples of cyclic alkyl groups include without limitation, cyclopropyl groups, cyclopentyl groups, cyclohexyl groups, etc.

As used herein, the abbreviation, "Me," refers to a methyl group; the abbreviation, "Et," refers to an ethyl group; the abbreviation, "Pr," refers to a propyl group; and the abbreviation, "iPr," refers to an isopropyl group.

DETAILED DESCRIPTION OF THE PREFERRED EMBODIMENTS

In an embodiment, a precursor for the deposition of a metal film comprises an organometallic compound having the formula: $(Op)_x(Cp)_y MR'_{2-x-y}$. As used herein, the term "organometallic" may refer to compounds or molecules that contain a metal-carbon bond. M may be any suitable metal. In particular, M may include any Group 11 metal such as without limitation, copper (Cu), silver (Ag) or gold (Au). Other suitable metals include ruthenium or tantalum. Op is a substituted or an unsubstituted open-pentadienyl ligand. Furthermore, Cp is a cyclopentadienyl ligand, which also may be substituted or unsubstituted. The subscript, x, is an integer representing the number of Op ligands, ranging from 0 to 1. The subscript, y, is an integer representing the number of Cp ligands, ranging from 0 to 1.

The R' substituent may be a functional group providing an even number of 7 electrons. Specifically, R' may be a C1 to C12 linear or branched alkyl group. Additionally, a may comprise trialkylsilyl groups, alkyl groups, alkylamide groups, alkoxide groups, alkylsilyl group, alkylsilylamide groups, amidinate groups, CO, $SiMe_2$, $SiEt_2$, $SiPr_2$, SiMeEt, SiMe(iPr), SiEt(iPr), $OMe_2$, $OEt_2$, tetrahydrofuran (THF), or combinations thereof. In embodiments where the organometallic compound comprises more than one R' groups, each R' group coupled to M may be the same or different from one another. In an exemplary embodiment, R' is bis((trimethylsilyl)acetylene. Other examples of suitable R' groups include without limitation, butadiene, butane, acetylene, cyclohexadiene, trimethylsilylacetylene, cyclohexa-1,4-diene, propylene, ethylene, etc.

According to one embodiment, the Cp ligand may have the following formula:

(1)

Alternatively, the Cp ligand may be represented by the formula: $CpR^{1-5}$. $R^1$-$R^5$ may each independently be a hydrogen group, a halogen group (e.g. Cl, Br, etc.), a C1-C4 linear or branched alkyl group, an alkylamide group, an alkoxide group, an alkylsilylamide group, an amidinate group, a carbonyl group, or combinations thereof. $R^{1-5}$ may be the same or different from one another. Examples of suitable Cp ligands include without limitation, methylcyclopentadiene, ethylcyclopentadiene, isopropylcyclopentadiene, and combinations thereof. In at least one embodiment, at least 4 of $R^{1-5}$ in the Cp ligand shown in formula (1) are hydrogen groups (i.e. unsubstituted).

In an embodiment, the Op ligand may have the following formula:

(2)

The Op ligand may alternatively be represented by the formula: $OpR^{1-7}$. $R^1$-$R^7$ may each independently be a hydrogen group, a halogen group (e.g. Cl, Br, etc.), a C1-C4 linear or branched alkyl group, an alkylamide group, an alkoxide group, an alkylsilylamide group, an amidinate group, a carbonyl group, or combinations thereof. $R^{1-7}$ may be the same or different from one another. Examples of Op ligands include without limitation, 1,3-pentadiene, 1,4-pentadiene, 3-methyl-1,3-pentadiene, 3-methyl-1,4-pentadiene, 2,4-dimethyl-1,3-pentadiene, 2,4-dimethyl-1,4-pentadiene, 3-ethyl-1,3-pentadiene, 1,5-bistrimethoxysilyl-1,3-pentadiene, and 1,5-bistrimethoxysilyl-1,4-pentadiene and combinations thereof. In at least one embodiment, at least 5 of $R^{1-7}$ in the Op ligand shown in formula (2) are hydrogen groups (i.e. unsubstituted).

In one embodiment, the precursor may be an organometallic compound having the formula:

(3)

In this embodiment, y equals 0. That is, the organometallic compound comprises only an open pentadienyl ligand and the R' ligand. Furthermore, in at least one embodiment, at least 5 of $R^{1-7}$ are hydrogen groups. In other words, besides the MR' functional group, the Op group has two substituents. The two substituents preferably are a methyl or ethyl group. In at least one embodiment, the precursor has the formula shown in (3) where R' is bis((trimethylsilyl)acetylene).

In one embodiment, the precursor may be an organometallic compound having the formula:

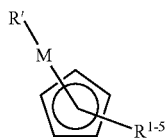

(4)

In this embodiment, x equals 0. That is, the organometallic compound comprises only a cyclopentadienyl ligand and the R' ligand. Furthermore, in at least one embodiment, at least 4 of $R^{1-5}$ are hydrogen groups. That is, besides the MR' functional group, the Cp group has only a single substituent. The single substituent preferably is a methyl or ethyl group. In at least one embodiment, the precursor has the formula shown in (4) where R' is bis((trimethylsilyl)acetylene).

Generally, the disclosed metal precursors have a low melting point. In at least one embodiment, the metal precursor is liquid at room temperature (e.g. ~25° C.). Specifically, embodiments of the precursors may have melting points less than about 50° C., alternatively less than about 40° C., alternatively less than about 35° C.

Examples of the disclosed precursors containing Cu include without limitation, CuCp(ethylene), Cu(MeCp)(ethylene), Cu(EtCp)(ethylene), Cu(iPrCp)(ethylene), CuCp(propylene), Cu(MeCp)(propylene), Cu(EtCp)(propylene), Cu(iPrCp)(propylene), CuCp(1-butene), Cu(MeCp)(1-butene), Cu(EtCp)(1-butene), Cu(iPrCp)(2-butene), CuCp(2-butene), Cu(MeCp)(2-butene), Cu(EtCp)(2-butene), Cu(iPrCp)(2-butene), CuCp(butadiene), Cu(MeCp)(butadiene), Cu(EtCp)(butadiene), Cu(iPrCp)(butadiene), CuCp(cyclobutadiene), Cu(MeCp)(cyclobutadiene), Cu(EtCp)(cyclobutadiene), Cu(iPrCp)(cyclobutadiene), CuCp (cyclohexa-1,3-ene), Cu(MeCp) (cyclohexa-1,3-diene), Cu(EtCp)(cyclohexa-1,3-diene), Cu(iPrCp)(cyclohexa-1,3-diene), CuCp(cyclohexa-1,4-diene), Cu(MeCp)(cyclohexa-1,4-diene), Cu(EtCp)(cyclohexa-1,4-diene), Cu(iPrCp)(cyclohexa-1,4-diene), CuCp(acetylene), Cu(MeCp)(acetylene), Cu(EtCp) (acetylene), Cu(iPrCp)(acetylene), CuCp(trimethylsilylacetylene), Cu(MeCp)(trimethylsilylacetylene), Cu(EtCp)(trimethylsilylacetylene), Cu(iPrCp)(trimethylsilylacetylene), CuCp (bis(trimethylsilyl)acetylene), Cu(MeCp)(trimethylsilylacetylene), Cu(EtCp)(bis(trimethylsilyl) acetylene), Cu(iPrCp)(bis(trimethylsilyl) acetylene), CuCp(ethylene), Cu(MeCp)(ethylene), Cu(EtCp) (ethylene), Cu(iPrCp)(ethylene), CuCp (trimethylvinylsilane), Cu(MeCp) (trimethylvinylsilane), Cu(EtCp)(trimethylvinylsilane), Cu(iPrCp)(trimethylvinylsilane), CuCp(bis (trimethylsilyl)acetylene), Cu(MeCp)(bis (trimethylsilyl)ethylene), Cu(EtCp)(bis (trimethylsilyl) ethylene), Cu(iPrCp)(bis(trimethylsilyl)ethylene), Cu(2,4-dimethylpentadienyl) (ethylene), Cu(2,4-dimethylpentadienyl)(propylene), Cu(2,4-dimethylpentadienyl)(1-butylene), Cu(2,4-dimethylpentadienyl)(2-butylene), Cu(2,4-dimethylpentadienyl)(butadiene), Cu(2,4-dimethyl pentadienyl)(cyclobutadiene), Cu(2,4-dimethylpentadienyl)(cyclohexa-1,3-diene), Cu(2,4-di methylpentadienyl)(cyclohexa-1,4-diene), Cu(2,4-dimethylpentadienyl)(acetylene), Cu(2,4-dimethylpentadienyl)(trimethylsilylacetylene), Cu(2,4-dimethylpentadienyl)(bis(trimethylsilyl) acetylene), or combinations thereof.

Examples of the disclosed precursors containing Ag include without limitation, AgCp(ethylene), Ag(MeCp)(ethylene), Ag(EtCp)(ethylene), Ag(iPrCp)(ethylene), AgCp (propylene), Ag(MeCp)(propylene), Ag(EtCp)(propylene), Ag(iPrCp)(propylene), AgCp(1-butene), Ag(MeCp)(1-butene), Ag(EtCp)(1-butene), Ag(iPrCp)(2-butene), AgCp (2-butene), Ag (MeCp)(2-butene), Ag(EtCp)(2-butene), Ag(iPrCp)(2-butaene), AgCp(butadiene), Ag(MeCp) (butadiene), Ag(EtCp)(butadiene), Ag(iPrCp)(butadiene), AgCp (cyclobutadiene), Ag(MeCp) (cyclobutadiene), Ag(EtCp) (cyclobutadiene), Ag(iPrCp)(cyclobutadiene), AgCp (cyclohexa-1,3-diene), Ag(MeCp) (cyclohexa-1,3-diene), Ag(EtCp)(cyclohexa-1,3-diene), Ag(iPrCp)(cyclohexa-1,3-diene), AgCp(cyclohexa-1,4-diene), Ag(MeCp)(cyclohexa-1,4-diene), Ag(EtCp)(cyclohexa-1,4-diene), Ag(iPrCp)(cyclohexa-1,4-diene), AgCp(acetylene), Ag(MeCp) (acetylene), Ag(EtCp) (acetylene), Ag(iPrCp)(acetylene), AgCp(trimethylsilylacetylene), Ag(MeCp) (trimethylsilylacetylene), Ag(EtCp)(trimethylsilylacetylene), Ag(iPrCp) (trimethylsilylacetylene), AgCp(bis(trimethylsilyl)acetylene), Ag(MeCp)(bis(trimethylsilyl)ethylene), Ag(EtCp) (bis (trimethylsilyl)acetylene), Ag(iPrCp)(bis(trimethylsilyl) acetylene), AgCp(trimethylvinyl silane), Ag(MeCp) (trimethylvinylsilane), Ag(EtCp)(trimethylvinylsilane), Ag(iPrCp) (trimethylvinylsilane), AgCp(bis(trimethylsilyl) acetylene), Ag(MeCp)(bis(trimethylsilyl) ethylene), Ag(EtCp)(bis(trimethylsilyl)ethylene), Ag(iPrCp)(bis(trimethylsilyl) ethylene), Ag(2,4-dimethylpentadienyl)(ethylene), Ag(2,4-dimethylpentadienyl)(propylene), Ag(2,4-dimethyl pentadienyl)(1-butylene), Ag(2,4-dimethylpentadienyl)(2-butylene), Ag(2,4-dimethylpentadienyl) (butadiene), Ag(2,4-dimethylpentadienyl)(cyclobutadiene), Ag(2,4-dimethylpentadienyl) (cyclohexadi-1,3-ene), Ag(2,4-dirnethylpentadienyl)(cyclohexadi-1,4-ene), Ag(2,4-dimethyl pentadienyl)(acetylene), Ag(2,4-dimethylpentadienyl)(trimethylsilylacetylene), Ag(2,4-dimethyl pentadienyl)(bis(trimethylsilyl)acetylene), or combinations thereof. Examples of the disclosed precursors containing Au include without limitation, AuCp(ethylene), Au(MeCp)(ethylene), Au(EtCp)(ethylene), Au(iPrCp)(ethylene), AuCp(propylene), Au(MeCp)(propylene), Au(EtCp)(propylene), Au(iPrCp)(propylene), AuCp(1-butene), Au(MeCp)(1-butene), Au(EtCp)(1-butene), Au(iPrCp)(2-butene), AuCp(2-butene), Au(MeCp)(2-butene), Au(EtCp)(2-butene), Au(iPrCp)(2-butene), AuCp(butadiene), Au(MeCp)(butadiene), Au(EtCp)(butadiene), Au(iPrCp)(butadiene), AuCp(cyclobutadiene), Au(MeCp)(cyclobutadiene), Au(EtCp)(cyclobutadiene), Au(iPrCp)(cyclobutadiene), AuCp (cyclohexa-1,3-diene), Au(MeCp)(cyclohexa-1,3-diene), Au(EtCp)(cyclohexa-1,3-diene), Au (iPrCp)(cyclohexa-1,3-diene), AuCp(cyclohexa-1,4-diene), Au(MeCp)(cyclohexa-1,4-diene), Au(EtCp)(cyclohexa-1,4-diene), Au(iPrCp)(cyclohexa-1,4-diene), AuCp(acetylene), Au(MeCp) (acetylene), Au(EtCp)(acetylene), Au(iPrCp)(acetylene), AuCp(trimethylsilylacetylene), Au (MeCp)(trimethylsilylacetylene), Au(EtCp)(trimethylsilylacetylene), Au(iPrCp)(trimethylsilyl acetylene), AuCp(bis(trimethylsilyl)acetylene), Au(MeCp)(bis(trimethylsilyl)ethylene), Au(EtCp) (bis(trimethylsilyl)acetylene), Au(iPrCp)(bis(trimethylsilyl)acetylene), AuCp(trimethylvinyl silane), Au(MeCp)(trimethylvinylsilane), Au(EtCp)(trimethylvinylsilane), Au(iPrCp) (trimethylvinylsilane), AuCp(bis(trimethylsilyl)acetylene), Au(MeCp)(bis(trimethylsilyl)ethylene), Au(EtCp)(bis(trimethylsilyl)ethylene), Au(iPrCp)(bis(trimethylsilyl)ethylene), Au(2,4-dimethyl pentadienyl)(ethylene), Au(2,4-dimethylpentadienyl)(propylene), Au(2,4-dimethylpentadienyl)(1-butylene), Au(2,4-dimethylpentadienyl)(2-butylene), Au(2,4-dimethylpentadienyl)(butadiene), Au(2,4-dimethylpentadienyl)(cyclobutadiene), Au(2,4-dimethylpentadienyl)(cyclohexadi-1,3-ene), Au(2,4-dimethylpentadienyl)(cyclohexadi-1,4-ene), Au(2,4-dimethylpentadienyl)(acetylene), Au(2,4-dimethylpentadienyl)(trimethylsilylacetylene), Au(2,4-dimethylpentadienyl)(bis(trimethyl silyl)acetylene), or combinations thereof.

The disclosed precursor compounds may be deposited using any deposition methods known to those of skill in the art. Examples of suitable deposition methods include without limitation, conventional CVD, low pressure chemical vapor deposition (LPCVD), atomic layer deposition (ALD), pulsed chemical vapor deposition (P-CVD), plasma enhanced atomic layer deposition (PE-ALD), or combinations thereof. In an embodiment, a first precursor may be introduced into a reaction chamber. The reaction chamber may be any enclosure or chamber within a device in which deposition methods take place such as without limitation, a cold-wall type reactor, a hot-wall type reactor, a single-wafer reactor, a multi-wafer reactor, or other types of deposition systems under conditions suitable to cause the precursors to react and form the layers. The first precursor may be introduced into the reaction chamber by bubbling an inert gas (e.g. $N_2$, He, Ar, etc.) into the precursor and providing the inert gas plus precursor mixture to the reactor.

Generally, the reaction chamber contains one or more substrates on to which the metal layers or films will be deposited. The one or more substrates may be any suitable substrate used in semiconductor manufacturing. Examples of suitable substrates include without limitation, silicon substrates, silica substrates, silicon nitride substrates, silicon oxy nitride substrates, tungsten substrates, or combinations thereof. Additionally, substrates comprising tungsten or noble metals (e.g. platinum, palladium, rhodium or gold) may be used.

In an embodiment, a method of depositing a metal film on substrate may further comprise introducing a second precursor into the reaction chamber. The second precursor may be a metal precursor containing one or more metals other than a Group 11 metal. For example, the second precursor may include without limitation, Mg, Ca, Zn, B, Al, In, Si, Ge, Sn, Ti, Zr, Hf, V, Nb, Ta, or combinations thereof. Other examples of metals include rare earth metals and lanthanides. The second precursor may contain silicon and/or germanium. In particular, examples of suitable second metal precursors include without limitation, trisilylamine, silane, disilane, trisilane, bis(tertiary-butylamino)silane (BTBAS), bis(diethylamino)silane (BDEAS), or combinations thereof. In addition, the second metal precursor may be an aminosilane having the formula: $SiH_x(NR^1R^2)_{4-x}$. The subscript, x, is an integer between 0 and 4. $R^1$ and $R^2$ may each independently be a hydrogen group or a C1-C6 alkyl group, either linear, branched, or cyclic. $R^1$ and $R^2$ may be the same or different from on another. In one embodiment, the second metal precursor is tris(diethylamino)silane (TriDMAS).

In an alternative embodiment, the second precursor may be an aluminum source. Examples of suitable aluminum sources include without limitation, trimethylaluminum, dimethylaluminum hydride, or combinations thereof. Additionally, the aluminum source may be an amidoalane having the formula: $AlR^1_x(NR^2R^3)_{3-x}$. The subscript, x, is an integer from 0 and 3. $R^1$, $R^2$, and $R^3$ may each independently be a hydrogen group or a C1-C6 carbon chain, either linear, branched or cyclic and may each be the same or different from on another.

In another embodiment, the second precursor may be a tantalum and/or niobium source selected from the group comprising $MCl_5$ and corresponding adducts, $M(NMe_2)_5$, $M(NEt_2)_4$, $M(NEt_2)_5$, or combinations thereof. M represents either tantalum or niobium. Furthermore, the tantalum and/or niobium source may be an amino-containing tantalum and/or niobium source having the formula: $M(=NR^1)(NR^2R^3)_3$. $R^2$, and $R^3$ may each independently be a hydrogen group or a C1-C6 alkyl group, either linear, branched, or cyclic. Generally, the weight ratio of the first metal precursor to the cobalt precursor introduced into the reaction chamber may range from about 100:1 to about 1:100, alternatively from about 50:1 to about 1:50, alternatively from about 1:1 to about 10:1.

In embodiments, the reaction chamber may be maintained at a pressure ranging from about 1 Pa to about 100,000 Pa, alternatively from about 10 Pa to about 10,000 Pa, alternatively from about 25 Pa to about 1000 Pa. In addition, the temperature within the reaction chamber may range from about 100° C. to about 500° C., alternatively from about 120° C. to about 450° C., alternatively from about 150° C. to about 350° C. Furthermore, the deposition of the metal film may take place in the presence of a hydrogen source. Thus, a hydrogen source may be introduced into the reaction chamber. The hydrogen source may be a fluid or a gas. Examples of suitable hydrogen sources include without limitation, $H_2$, $H_2O$, $H_2O_2$, $N_2$, $NH_3$, hydrazine and its alkyl or aryl derivatives, diethylsilane, trisilylamine, silane, disilane, phenylsilane and any molecule containing Si—H bonds, dimethylaluminum hydride, hydrogen-containing radicals such as H˙, OH˙, N˙, NH˙, $NH_2$˙, or combinations thereof. In further embodiments, an inert gas may be introduced into the reaction chamber. Examples of inert gases include without limitation, He, Ar, Ne, or combinations thereof. A reducing fluid may also be introduced in to the reaction chamber. Examples of suitable reducing fluids include without limitation, carbon monoxide, $Si_2Cl_6$, or combinations thereof.

The metal precursors may be introduced sequentially (as in ALD) or simultaneously (as in CVD) into the reaction chamber. In one embodiment, the first and second precursors may be pulsed sequentially or simultaneously (e.g. pulsed CVD) into the reaction chamber while the oxidizing or nitridizing gas is introduced continuously into the reaction chamber. Each pulse of the cobalt and/or first metal precursor may last for a time period ranging from about 0.01 s to about 10 s, alternatively from about 0.3 s to about 3 s, alternatively from about 0.5 s to about 2 s. In another embodiment, the reaction fluid, and/or the inert gas may also be pulsed into the reaction chamber. In such embodiments, the pulse of each gas may last for a time period ranging from about 0.01 s to about 10 s, alternatively from about 0.3 s to about 3 s, alternatively from about 0.5 s to about 2 s.

While embodiments of the invention have been shown and described, modifications thereof can be made by one skilled in the art without departing from the spirit and teachings of the invention. The embodiments described and the examples provided herein are exemplary only, and are not intended to be limiting. Many variations and modifications of the invention disclosed herein are possible and are within the scope of the invention. Accordingly, the scope of protection is not limited by the description set out above, but is only limited by the claims which follow, that scope including all equivalents of the subject matter of the claims.

The discussion of a reference is not an admission that it is prior art to the present invention, especially any reference that may have a publication date after the priority date of this application. The disclosures of all patents, patent applications, and publications cited herein are hereby incorporated herein by reference in their entirety, to the extent that they provide exemplary, procedural, or other details supplementary to those set forth herein.

What is claimed is:

1. A method for depositing a metal film on to one or more substrates comprising:
   a) providing one or more substrates in a reaction chamber;
   b) introducing a first precursor into the reaction chamber, wherein the first precursor comprises an organometallic compound having the formula:

$(Op)_x(Cp)_yM$ wherein M is a group 11 metal, Op is an open-pentadienyl group, and Cp is a cyclopentadienyl group, wherein Op and Cp may each comprise functional groups selected from the group consisting of a hydrogen group, a halogen group, a C1-C4 alkyl group, an alkylamide group, an alkoxide group, an alkylsilylamide group, an amidinate group, a carbonyl group, and combinations thereof, and wherein x is 1 and y is 1; and
   c) vaporizing the first precursor to deposit the metal film on to the one or more substrates.

2. The method of claim 1, wherein introducing the first precursor and the second precursor into the reaction chamber comprises pulsing the first metal precursor and the second metal precursor into the reaction chamber.

3. The method of claim 1, wherein the first precursor is liquid at room temperature.

4. The method of claim 1, wherein the one or more substrates comprise silicon, silica, silicon nitride, silicon oxy nitride, tungsten, or combinations thereof.

5. The method of claim 1, wherein the reaction chamber is at a temperature ranging from about 150° C. to about 350° C. in (c).

6. The method of claim 1, wherein the reaction chamber is at a pressure ranging from about 1 Pa to about 1,000 Pa in (c).

7. The method of claim 1, further comprising introducing a second precursor into the reaction chamber.

8. The method of claim 7, wherein the second precursor comprises Mg, Ca, Zn, B, Al, In, Si, Ge, Sn, Ti, Zr, Hf, V, Nb, Ta, a lanthanide, a rare earth metal, or combinations thereof.

9. The method of claim 7, wherein the second precursor comprises trisilylamine, silane, disilane, trisilane, bis(tertiary-butylamino)silane (BTBAS), bis(diethylamino)silane (BDEAS), an aminosilane having the formula: $SiH_x(NR^1R^2)_{4-x}$, wherein x is an integer between 0 and 4, $R^1$ and $R^2$ may each independently be a hydrogen group or a C1-C6 alkyl group, and wherein $R^1$ and $R^2$ may be the same or different from one another, or combinations thereof.

10. The method of claim 7, wherein introducing the first precursor and the second precursor into the reaction chamber occurs simultaneously.

11. The method of claim 7, wherein introducing the first precursor and the second precursor into the reaction chamber occurs sequentially.

12. The method of claim 7, wherein the second precursor is an aluminum source.

13. The method of claim 12, wherein the aluminum source comprises trimethylaluminum, dimethylaluminum hydride, a compound having the formula:

$AlR^1_x(NR^2R^3)_{3-x}$ wherein x is an integer from 0 and 3, $R^1$, $R^2$, and $R^3$ may each independently be a hydrogen group or a C1-C6 alkyl group and $R^1$, $R^2$, and $R^3$ may each be the same or different from one another, or combinations thereof.

14. The method of claim 7, wherein the second precursor comprises a tantalum source or a niobium source.

15. The method of claim 14, wherein the tantalum source or niobium source comprises one or more compounds having the following formulas: $MCl_5$, $M(NMe_2)_5$, $M(NEt_2)_4$, $M(NEt_2)_5$, $M(=NR^1)(NR^2R^3)_3$, wherein $R^1$, $R^2$, and $R^3$ may each independently be a hydrogen group or a C1-C6 alkyl group, and wherein $R^1$, $R^2$, and $R^3$ may be the same or different from one another, wherein M is tantalum or niobium.

16. The method of claim 1, further comprising introducing hydrogen source, a reducing fluid, an inert gas, or combinations thereof into the reaction chamber.

17. The method of claim 16, wherein the hydrogen source comprises $H_2$, $H_2O$, $H_2O_2$, $N_2$, $NH_3$, hydrazine and its alkyl or aryl derivatives, diethylsilane, trisilylamine, silane, disilane, phenylsilane, dimethylaluminum hydride, H• radicals, OH• radicals, NH• radical, $NH_2$• radicals, or combinations thereof.

18. The method of claim 16, wherein the reducing fluid comprises carbon monoxide, $Si_2Cl_6$, or combinations thereof.

19. A precursor for depositing a metal film on to a substrate comprising:
   an organometallic compound having the formula:

$(Op)_x(Cp)_yM$ wherein M is a group 11 metal, Op is an open-pentadienyl group, and Cp is a cyclopentadienyl group,
   wherein Op and Cp may each comprise functional groups selected from the group consisting of a hydrogen group, a halogen group, a C1-C4 alkyl group, an alkylamide group, an alkoxide group, an alkylsilylamide group, an amidinate group, a carbonyl group, and combinations thereof, and wherein x is 1 and y is 1.

20. The precursor of claim 19, wherein Op has the formula: $OpR^{1-7}$, wherein $R^1$-$R^7$ may each independently be a hydrogen group, a halogen group, a C1-C4 alkyl group, an alkylamide group, an alkoxide group, an alkylsilylamide group, an amidinate group, a carbonyl group, or combinations thereof, and wherein $R^{1-7}$ may be the same or different from one another.

21. The precursor of claim 19, wherein Cp has the formula: $CpR^{1-5}$, wherein $R^1$-$R^5$ may each independently be a hydrogen group, a halogen group, a C1-C4 alkyl group, an alkylamide group, an alkoxide group, an alkylsilylamide group, an amidinate group, a carbonyl group, or combinations thereof, and wherein $R^{1-5}$ may be the same or different from one another.

22. The precursor of claim 19, wherein the organometallic compound has a melting point less than about 35° C.

* * * * *